United States Patent [19]
Huth et al.

[11] Patent Number: 5,503,000
[45] Date of Patent: Apr. 2, 1996

[54] METHOD FOR DETERMINING SMALL QUANTITIES OF CARBON MONOXIDE AND NITROGEN OXIDES IN GASEOUS MIXTURES

[75] Inventors: Gerhard Huth; Anton Kling, both of Gerlingen; Detlef Baresel, Stuttgart, all of Germany

[73] Assignee: Robert Bosch GmbH, Stuttgart, Germany

[21] Appl. No.: 244,262

[22] PCT Filed: Nov. 17, 1992

[86] PCT No.: PCT/DE92/00958

§ 371 Date: May 20, 1994

§ 102(e) Date: May 20, 1994

[87] PCT Pub. No.: WO93/10441

PCT Pub. Date: May 27, 1993

[30] Foreign Application Priority Data

Nov. 22, 1991 [DE] Germany .......................... 41 38 369.9

[51] Int. Cl.[6] .......................... G01N 31/00; G01N 27/00; H01C 7/00
[52] U.S. Cl. .................. 73/23.2; 422/83; 422/90
[58] Field of Search .................. 73/23.2, 31.06, 73/23.31, 23.32, 335.02, 23.2, 31.06; 340/634; 422/90, 98, 94, 83

[56] References Cited

U.S. PATENT DOCUMENTS

| | | | |
|---|---|---|---|
| 3,695,848 | 10/1972 | Taguchi | 73/31.06 |
| 4,030,340 | 6/1977 | Chang | 73/23 |
| 4,142,400 | 3/1979 | Colla et al. | 73/23 |
| 4,147,513 | 4/1979 | Bienkowski et al. | 23/232 |
| 4,198,850 | 4/1980 | Firth et al. | 73/23 |
| 4,399,684 | 8/1983 | Advani et al. | 73/1 G |
| 4,485,667 | 12/1984 | Lalauze et al. | 73/23 |
| 4,944,273 | 7/1990 | Baresel et al. | 123/440 |
| 5,222,388 | 6/1993 | Sinha et al. | 73/23.2 |
| 5,314,828 | 5/1994 | Dalla Betta et al. | 436/118 |
| 5,351,029 | 9/1994 | Huth et al. | 338/34 |

FOREIGN PATENT DOCUMENTS

92/13270  8/1992  WIPO .

Primary Examiner—Hezron E. Williams
Assistant Examiner—J. David Wiggins
Attorney, Agent, or Firm—Spencer & Frank

[57] ABSTRACT

The invention relates to a method for determining small quantities of carbon monoxide and nitrogen oxides in gaseous mixtures containing oxygen with the aid of a sensor whose electrical resistance changes at a higher temperature with the carbon monoxide and nitrogen oxide concentrations. It makes use of the fact that, with suitable sensors, on the one hand the resistance-temperature curve of the one of the gases to be determined is clearly different from that of the reference mixture over a broad temperature range (gaseous mixture without the two gases to be determined) and, on the other hand, the resistance-temperature curves of the two gases to be determined approach one another in one part of this temperature range, or coincide, and maintain a clear distance from one another in another part of this temperature range.

11 Claims, 1 Drawing Sheet

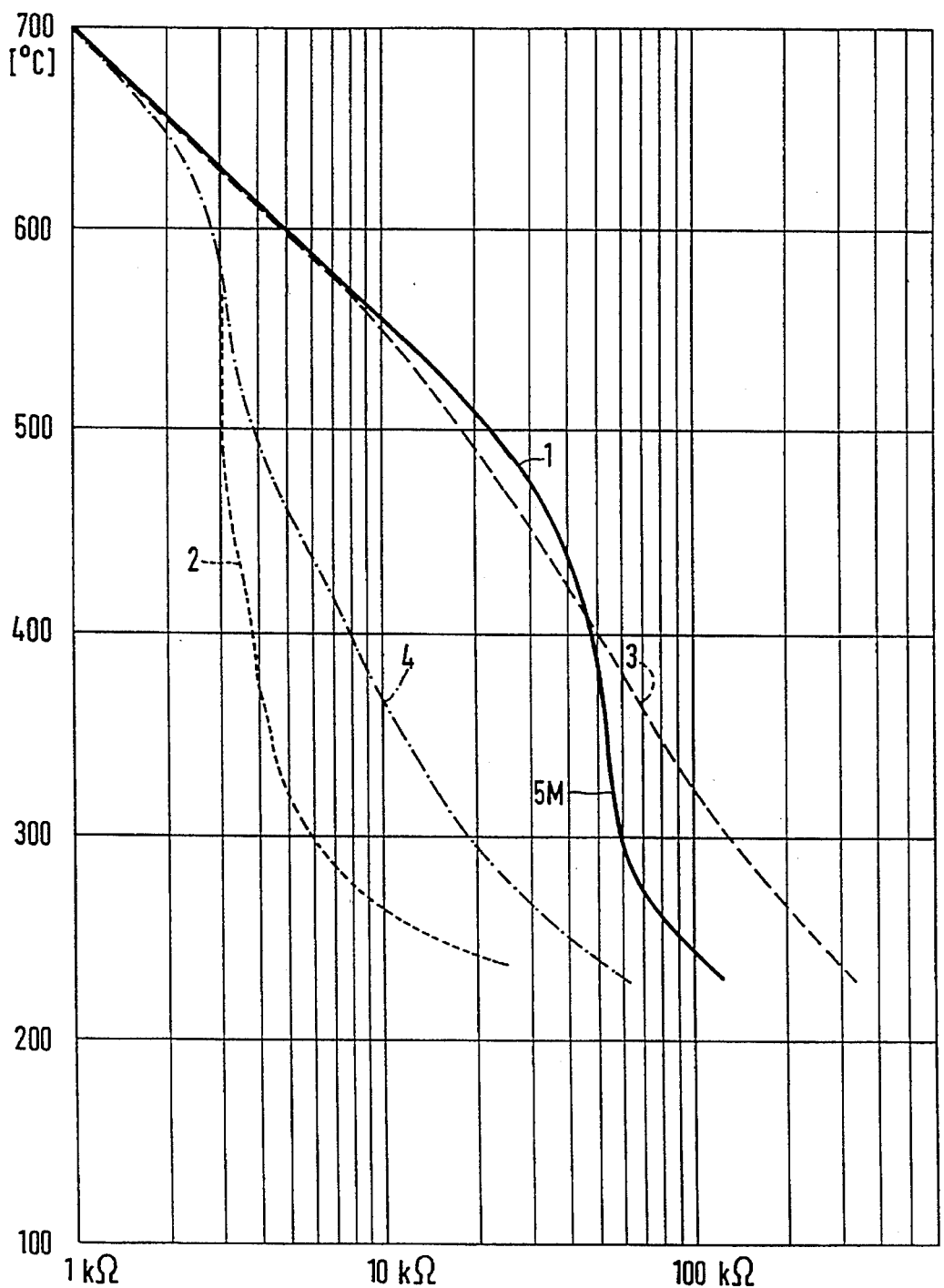

1

METHOD FOR DETERMINING SMALL QUANTITIES OF CARBON MONOXIDE AND NITROGEN OXIDES IN GASEOUS MIXTURES

BACKGROUND OF THE INVENTION

1. Field of the Invention

The invention relates to a method for determining small quantities of carbon monoxide and nitrogen oxides in gaseous mixtures containing oxygen with the aid of a sensor whose electrical resistance changes in a specific manner with the carbon monoxide and nitrogen oxide concentrations.

2. Description of the Related Art

In addition to nitrogen, oxygen and nonburned hydrocarbons, waste gases resulting from combustion processes frequently contain small quantities of carbon monoxide and nitrogen oxides and carbon dioxide resulting from combustion. These gases are pollutants in the sense of environmental protection, and must therefore be removed to the fullest possible extent. It is important to utilize methods that permit determination of the content of these gases in the gaseous mixtures in a simple manner and with sufficient accuracy.

SUMMARY OF THE INVENTION

The present invention provides a method for determining small quantities of carbon monoxide and nitrogen oxides in gaseous mixtures containing oxygen with the aid of a sensor whose electrical resistance changes at a higher temperature with the carbon monoxide and nitrogen oxide concentrations. The method is characterized in that (a) the change in resistance caused by the contact of the sensor with the gaseous mixture to be analyzed is measured at a first temperature $T_1$ in a temperature range in which the change in resistance by means of the one of the two gases is considerable, while the change caused by the other of the two gases is comparatively slight, and the concentration of this one of the two gaseous is thus determined, (b) the change in resistance due to this gas is measured at the previously determined concentration at a second temperature $T_2$ in a temperature range in which the two gases contribute significantly to the change in resistance, (c) the change in resistance caused by the gaseous mixture containing the two gases to be determined is measured at this second temperature $T_2$, and (d) the concentration of the other of the gases to be determined is determined from the difference in changes in resistance according to (b) and (c).

The method in accordance with the invention permits determination of each of the two named gases in a simple manner with sufficient percision for all practical purposes. Because the sensors react quickly, the values are available immediately. The method can be automated without difficulty, making it inexpensive and less susceptible to operating errors. The sensors have a long service life, even if the composition of gaseous mixtures changes constantly and the measuring temperature changes frequently, so the method is extremely well-suited for continuous duty. The sensors are small in dimension, and hence require little space.

BRIEF DESCRIPTION OF THE DRAWINGS

The sale drawing FIGURE gives variable point representation of the resistance-temperature function of a sensor operating in accordance with the method of the invention for different gaseous mixtures, namely 1. 20% oxygen, 80% nitrogen
2. 20% oxygen, 200 ppm carbon monoxide, remainder nitrogen
3. 20% oxygen, 50 ppm nitrogen monoxide, remainder nitrogen
4. 20% oxygen, 200 ppm carbon monoxide, 50 ppm nitrogen monoxide, remainder nitrogen
5. same gaseous mixture as listed in 1 above.

In the drawings and the following description, unless otherwise indicated the percentages are given in volume percent and the parts are in ppm parts by volume.

DESCRIPTION OF THE PREFERRED EMBODIMENT

The invention is particularly suited for determining carbon monoxide and nitrogen oxides in lean gaseous mixtures, i.e., mixtures that contain little carbon monoxide and nitrogen oxides and a comparatively large quantity of oxygen. The carbon monoxide content is generally between 1 and 10,000 ppm, particularly between 10 and 1000 ppm, and the nitrogen oxide content (i.e., nitrogen monoxide and nitrogen dioxide) is between 0.1 and 5000 ppm, particularly between 1 and 500 ppm. The oxygen content is generally between 0.1 and 15%, particularly between 1 and 6%. The remainder of the gaseous mixture is predominantly composed of nitrogen and carbon dioxide. Smaller quantities of nonburned hydrocarbons and sulfur dioxide can be present without interfering with the determination of carbon monoxide and nitrogen oxides.

Particularly suited for the method are sensors whose resistance-temperature characteristic for the two gases to be determined is in accordance with the drawing. This applies to a great extent to German Patent Application P 4,100, 915.0. The sensors are designed on a basis of an n-conducting metal oxide, such as tin (IV) oxide, that is doped with other metal oxides in such a manner that the oxidation of the carbon monoxide to carbon dioxide takes place at reduced speed. For example, tin (IV) oxide that is doped with 0.01 to 0.2 mol % magnesium oxide, 0.01 to 0.2 mol % palladium oxide and 0.001 to 0.1 mol % tantalum (V) oxide, is suitable.

The method of the invention is based on the observation that, when suitable sensors are used, the resistance-temperature curves of each individual gas of the two named gases (i.e., in the absence of the respective other gas) and the curve of the combination of the two gases in the gaseous mixture to be analyzed have a position relative to one another and with respect to the reference curve (gaseous mixture without the two gases to be determined) that is favorable for measurement. This is the case when the curve of one of the two gases to be determined remains at a clear distance from the reference curve over wide temperature ranges, and the curve of the combination of the two gases in the gaseous mixture approaches (or practically coincides with) the curve of this one of the two gases to be determined in one part of this temperature region, and maintains a clear distance from it in another part of the temperature range.

These conditions are fulfilled in a favorable manner by the mentioned sensors according to German Patent Application P 4,100,915.0. The measurements that produced the curves in the drawing were performed with a sensor whose active components had the following composition:

tin (IV) oxide with 0.1 mol % magnesium oxide 0.1 mol % palladium oxide
0.005 mol % tantalum (V) oxide The applicable values for this sensor are those that were measured with a measuring current of 1 mA. Curve 1 is the reference curve for "synthetic" air, and was measured with an increasing temperature. Curve 5, measured in the same medium but with a falling temperature, coincides with curve 1. Therefore, there are no hysteresis that could adulterate the measurements. Curve 2 shows by way of clear deviations from curve 1 that small quantities of carbon monoxide cause considerable changes in resistance in the range between approximately 250° C. and approximately 600° C. In contrast, the influence of the nitrogen monoxide alone is slight, at least in the temperature range between approximately 400° C. and approximately 700° C., where curves 1 and 3 practically coincide. Curve 4 represents the measurements with small quantities of carbon monoxide and nitrogen monoxide, and approaches the carbon monoxide curve 2 in the temperature range between approximately 500° C. and approximately 600° C. In this range the change in resistance due to nitrogen monoxide is comparatively slight; this range is thus suited for sufficiently precise determination of carbon monoxide from only one measurement in the named temperature range. In contrast, curves 2 and 4 are clearly different in the temperature range of approximately 250° C. to approximately 400° C., i.e. the two gases contribute significantly to the change in resistance. Therefore, at a temperature in this range, on the one hand the change in resistance caused by the carbon monoxide alone can be measured, the concentration of which is known from the first measurement at a higher temperature, and on the other hand, the change in resistance caused by the two gases together can be measured. The deviation in the two measured values is a measure for the nitrogen monoxide concentration.

Hence, a determination of the two gases can be performed in succession in a simple manner, namely with 3 measurements at 2 different temperatures. Because the sensors react very quickly (within the millisecond range), the time requirement is low. If a number of measurements is to be expected over an extended period of time, the measured resistance values can be converted into the desired concentrations with the aid of an appropriate computer, thus saving further expense of intellectual energy. A series of measurements is required of the changes in resistance of the gaseous mixtures with the one and then both of the gases to be determined at the desired measuring temperature, which series produces an unequivocal connection between the measured values and the nitrogen concentration.

The precision of the measurements can be increased if an inhibitor is additionally used that slows the reaction

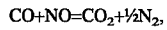
$CO+NO=CO_2+\frac{1}{2}N_2$, which adulterates the measured result. Inhibitors of this type are, for example, manganese (II) oxide and chromium (III) oxide. They can be added to the tin (IV) oxide of the sensor, or be placed before it as a separate inhibitor layer. Two sensors would then be needed, one with the inhibitor and the other without, whose signals must be received and processed separately. An appropriate computing program then supplies the purified concentrations of the two gases, which take into account the error caused by the mentioned reaction.

What is claimed is:

1. A method for determining small quantities of carbon monoxide and nitrogen oxides in a gaseous mixture containing oxygen with the aid of a metal oxide sensor whose electrical resistance changes with temperature in proportion to the carbon monoxide and nitrogen oxide concentrations, the method comprising the step of:

(a) contacting the metal oxide sensor with the gaseous mixture;

(b) heating the metal oxide sensor to a first temperature ranging between 400° C. to 600° C.;

(c) measuring the change in electrical resistance of the metal oxide sensor at the first temperature to provide a first measured value, R1, thereby to determine an electrical resistance change value representative of the carbon monoxide concentration;

(d) setting the temperature of the metal oxide sensor at a second temperature ranging between 250° C. and 400° C.;

(e) measuring the change in electrical resistance of the metal oxide sensor at the second temperature to provide a second measured value, R2, and thereby to determine an electrical resistance change value representative of the carbon monoxide and nitrogen oxide concentrations; and (f) determining the difference between the first and second measured values R1 and R2, and thereby to determine by subtraction an electrical resistance change value, R3, representative of the concentration of the nitrogen oxides.

2. The method as defined in claim 1, wherein the metal oxide sensor is comprised of an n-conductive metal oxide layer doped with other metal oxides such that the oxidation of the carbon monoxide to carbon dioxide takes place at a reduced speed, thereby preserving sensor response and sensor sensitivity to carbon monoxide and nitrogen oxides concentrations.

3. The method as defined in claim 2, wherein the metal oxide sensor is comprised of tin (IV) oxide doped with 0.01 to 0.2 mol % magnesium oxide, 0.01 to 0.2 mol % palladium oxide and 0.001 to 0.1 mol % tantalum (V) oxide.

4. The method as defined in claim 1, further comprising the step of including in the metal oxide sensor an inhibitor for additionally slowing the reaction $CO+NO=CO_2+\frac{1}{2}N_2$ so as to increase the accuracy of said first and second measured values.

5. The method as defined in claim 2, further comprising the step of including in the metal oxide sensor an inhibitor for additionally slowing the reaction $CO+NO=CO_2+\frac{1}{2}N_2$ so as to increase the accuracy of said first and second measured values.

6. The method as defined in claim 3, further comprising the step of including in the metal oxide sensor an inhibitor for additionally slowing the reaction $CO+NO=CO_2+\frac{1}{2}N_2$ so as to increase the accuracy of said first and second measured values.

7. The method as defined in claim 4, further comprising providing first and second metal oxide sensors, the first metal oxide sensor including the inhibitor and the second metal oxide sensor not including the inhibitor.

8. The method as defined in claim 7, wherein the inhibitor is included in the metal oxide sensor by adding the inhibitor to the metal oxide of the metal oxide layer sensor.

9. The method as defined in claim 7, wherein the inhibitor is included in the metal oxide sensor by disposing the inhibitor on the metal oxide of the metal oxide sensor as a separate inhibitor layer.

10. The method as defined in claim 1, wherein the inhibitor is selected from the group consisting of manganese (II) oxide and chromium (III) oxide.

11. The method as defined in claim 1, further comprising converting the first measured value, R1, into a concentration value for the carbon monoxide by comparing the first measured value, R1, to a pre-determined, calibrated carbon monoxide reference curve and converting the electrical resistance change value, R3, into a concentration value for the nitrogen oxides by comparing the subtracted electrical resistance change value, R3, to a pre-determined, calibrated nitrogen oxides reference curve.

* * * * *